United States Patent [19]

Rudler

[11] 4,295,828
[45] Oct. 20, 1981

[54] EJECTOR HOLDER FOR SYRINGE-TYPE CARTRIDGE

[75] Inventor: Helmut Rudler, York, Pa.

[73] Assignee: Dentsply Research & Development Corp., Milford, Del.

[21] Appl. No.: 190,681

[22] Filed: Sep. 25, 1980

[51] Int. Cl.$^3$ .............................................. A61C 5/04
[52] U.S. Cl. ........................................................ 433/90
[58] Field of Search ................ 433/90, 89; 222/326, 222/570, 567; 285/320, 315, 316, 86; 128/234

[56] References Cited

U.S. PATENT DOCUMENTS

| | | | |
|---|---|---|---|
| 3,454,047 | 7/1969 | Johnston | 285/86 |
| 3,581,399 | 6/1971 | Dragan | 433/90 |
| 4,188,724 | 2/1980 | Lichon | 433/90 |
| 4,198,756 | 4/1980 | Dragan | 433/90 |

FOREIGN PATENT DOCUMENTS 535175 12/1930 Fed. Rep. of Germany ........ 433/90

Primary Examiner—Robert Peshock
Attorney, Agent, or Firm—C. Hercus Just

[57] ABSTRACT

A manually-operable ejector holder for a loaded syringe-type cartridge having an annular collar on one end and a discharge tip on the other end and including an elongated barrel having a piston slidable therein and actuated by a fixed handle on one end of the barrel and a pivoted operating lever cooperable with the handle. The opposite end of the barrel has a curved transverse recess to receive a portion of the collar on the cartridge and a pivoted locking member has a corresponding curved transverse recess in opposition to and cooperable with the recess in the opposite end of said barrel to receive an opposite portion of the collar on the cartridge, and a sleeve is slidable over said locking member and along said opposite end of said barrel to detachably connect said cartridge to said holder.

6 Claims, 6 Drawing Figures

EJECTOR HOLDER FOR SYRINGE-TYPE CARTRIDGE

BACKGROUND OF THE INVENTION

In recent years it has become popular to package various types of material, especially medicinal or quasi-medicinal types in sealed cartridges, insertable in a suitable type of holder and/or ejector device, for purposes of preserving purity of the medicament and the like, insuring a patient of accurately measured quantities, as well as minimizing effort now required in introducing bulk amounts of material in a syringe and ejecting measured quantities thereof, for example. Various previous efforts in this direction are illustrated and described in various prior U.S. patents, particularly U.S. Pat. No. 3,581,399 to Dragan, dated June 1, 1971, in which a typical example of loaded cartridge is illustrated in conjunction with one type of holder and discharge device. The present invention primarily comprises an improvement over this particular patented structure.

Other efforts have been made to produce similar devices, one of these comprising the subject matter of prior U.S. Pat. No. 3,900,954, also to Dragan, dated Aug. 26, 1975, and comprising a simpler version than in Dragan's '399 patent.

Still further, prior U.S. Pat. No. 2,917,830 to Cerveris, dated Dec. 22, 1959; No. 3,521,356 to Newman, dated July 21, 1970; and No. 3,854,209 to Franklin et al, dated Dec. 17, 1974 illustrate still other efforts and in which, for example, it will be seen in the Newman and Franklin et al patents that bayonet slots have been employed to secure a cap to a barrel member for purposes of holding a cartridge upon one end of the barrel. The Cerveris patent has a pivoted supporting member for the cartridge, which is held in association with the barrel by means of a pivoted latch.

For one reason or another, these foregoing efforts are susceptible to improvement, and the present invention constitutes such an improvement for the reasons set forth below.

SUMMARY OF THE INVENTION

It is among the principal objects of the invention to provide an ejector holder for a syringe-type cartridge which is susceptible of very secure, yet rapid, operation for purposes of attaching to one end of the holder a cartridge which has a circular shoulder at one end adapted to be mounted within recesses in one end of the holder and said recesses are separable to permit removal or attachment of the cartridge to the holder by the annular collar thereon being received within the recesses or separable therefrom.

Another object of the invention is to provide cartridge attaching means on one end of the holder which is in the nature of a pair of similar semi-circular members in cross-section, one being fixed upon the holder and the other being movable toward and from the fixed one, and both of them having complementary transverse curved recesses therein to receive the annular collar on the cartridge, and the holder also including slidable means to secure the relatively movable attaching means in clamped position around the collar of the cartridge.

One further object of the invention is to provide said aforementioned securing means in the form of a cylindrical sleeve slidable longitudinally upon the barrel between clamping and unclamping positions and, when said sleeve is disposed in clamped position, it encircles the two relatively movable attaching means on the end of the barrel which, when in said clamping position, are circular in cross-section and such simple securing means therefor effectively holds the cartridge firmly attached to the barrel which is in the nature of a syringe body of conventional syringes.

Still another object of the invention is to provide on the end of the barrel opposite the cartridge supporting end, a handle which extends transverse to the axis of the barrel and is somewhat is the nature of a pistol-grip handle and associated therewith is a pivoted lever-type member, which is associated with the handle in such manner that the end of the plunger which projects outwardly from the end of the barrel to which the handle is attached, is engaged by said pivoted lever member and when squeezed toward the handle, it effectively and powerfully projects the opposite end of the plunger into the end of the cartridge upon which the annular collar is mounted to force the contents of the cartridge from the tip thereof, said plunger also including a compression coil spring surrounding the same to restore the plunger to the outermost position thereof.

Details of the foregoing objects and of the invention, as well as other objects thereof are set forth in the following specification and illustrated in the accompanying drawing comprising a part thereof.

DETAILED DESCRIPTION

Figure 1:
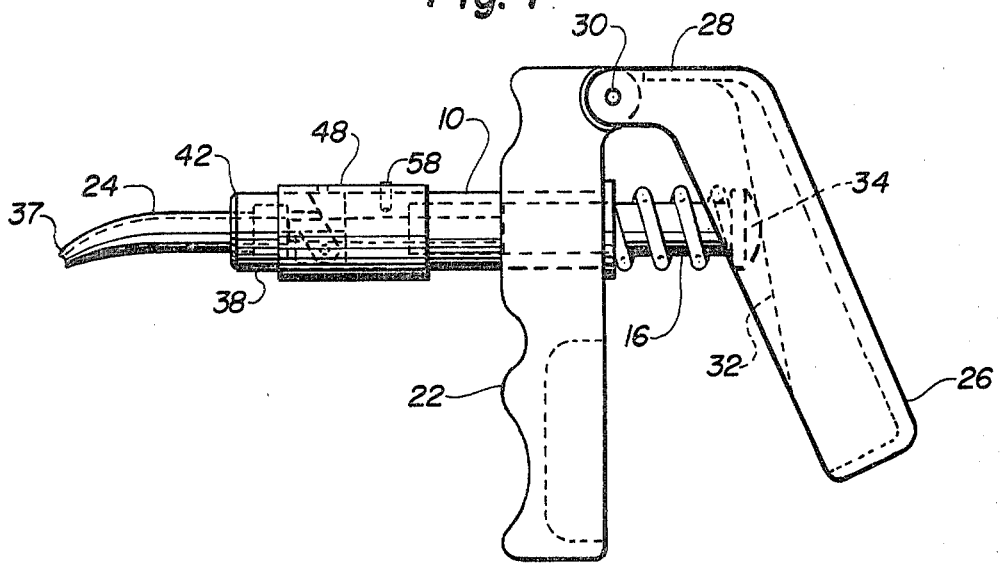
FIG. 1 is a side elevation of the ejector holder comprising the principles of the present invention, and also showing a typical syringe-type cartridge connected to one end thereof.
Figure 2:
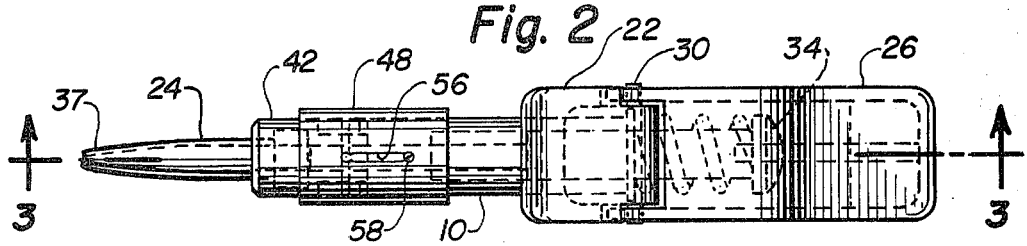
FIG. 2 is a top plan view of the ejector holder and cartridge shown in FIG. 1.
Figure 3:
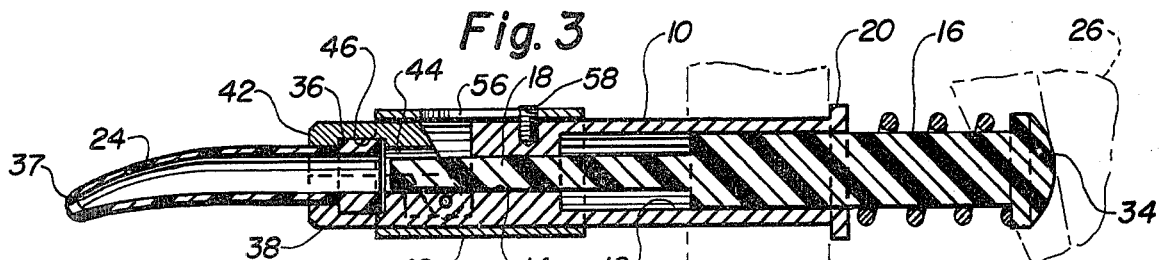
FIG. 3 is a vertical sectional view of the ejector holder and the cartridge shown in FIG. 2, as seen on the line 3—3 thereof and illustrated on a larger scale than employed in FIGS. 1 and 2, portions of the handle and operating mechanism being shown fragmentarily in phantom in FIG. 3.

The preferred embodiment of the ejector holder comprising the principles of the present invention is illustrated in side elevation in FIG. 1 and in top plan view in FIG. 2. In these figures, it will be seen that the holder comprises a cylindrical barrel 10 which has an interior bore of two different diameters, the bore 12, best shown in FIG. 3, is of a larger diameter than the forward bore 14, for purposes of respectively receiving two different portions of a plunger 16, which has a diameter complementary to the larger bore 12, while the forward projecting end 18 of plunger 16 is of smaller diameter and is slidable within the forward bore 14 of smaller diameter than bore 12. The plunger 16 of larger diameter has an outer end that projects a limited distance beyond the outer end 20 of barrel 10 and said outer end of the barrel also is formed in the nature of a circular flange for purposes of being abutted by a transverse handle 22, comprising one member of manually-engageable means for operating the plunger. Preferably, however, the handle member 22 is fixed with respect to barrel 10.

For purposes of moving the barrel 16, 18 forwardly toward a cartridge 24, which is firmly and quickly connectable to and removable from the forward end of barrel 10, handle 22 has associated therewith an operating lever 26, which is pivotally attached to the upper end of handle 22 and said lever preferably includes a laterally offset end 28, which is the portion thereof actually pivotally connected to the upper end of handle 22 by means of a pivot pin 30, which extends between complementary, aligned holes respectively in the handle 22 and operating lever 26. Further, the portion of the operating lever 26, which is nearest handle 22 is provided on the interior thereof with a recess defined by a ramp or cam surface 32, which is provided to facilitate the operation of the lever 32 with respect to the projecting outer end of plunger 16 that terminates in a rounded button 34 that actually is slidably engaged by the ramp surface 32.

Figure 4:
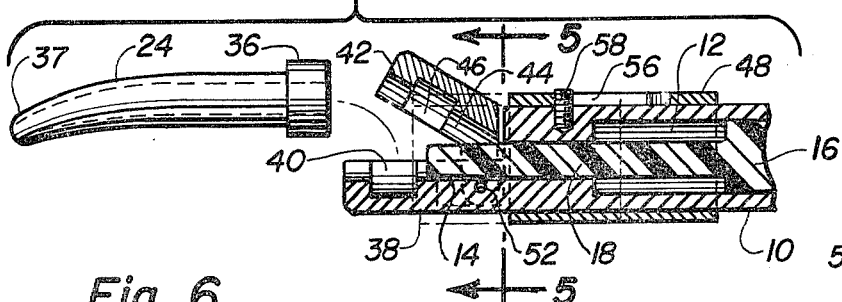
FIG. 4 is a fragmentary vertically-sectioned view illustrating the cartridge attaching end portion of the holder with the cartridge separated therefrom and the attaching members of the holder being in separated position for removal or attachment of the cartridge thereto.
Figure 6:
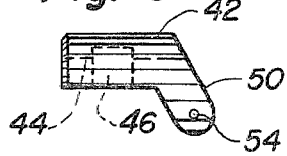
FIG. 6 is a small side elevation of the movable attaching member per se, which is shown in elevated position in FIG. 4 and in closed, locking position in FIG. 3.

The principal improvement afforded by the present invention comprises the means on the forward end of the barrel 10 by which the cartridge 24 is quickly and firmly connectable to and removable from the barrel 10. Said cartridge is of the type that contains materials, such as measured quantity of medicament, filling material, cement or otherwise, and at one end, said cartridge has an annular collar 36 integrally formed therewith, as best shown in FIGS. 3 and 4, and the opposite forward end is adapted to be ruptured or broken to comprise a discharge tip 37 through which the material contained in the cartridge is discharged when the plunger 16, 18 is moved forwardly by compressing the operating lever 26 toward the handle 22 in manual fashion. The forward end of the barrel 10 is formed with a cutout portion extending longitudinally rearward from the forward end for about half the diameter of the barrel 10 and thereby forming a semi-cylindrical projecting forward end 38, which has a curved transverse recess 40 therein and also approximately half of the forward bore 14. Associated with the projecting end 38 of the barrel is a locking member 42 which is complementary in shape for the major portion of the same to the projecting end 38 of barrel 10 and has a semi-circular longitudinally extending recess 44, which is complementary to the half of the bore 18 in projecting end 38. In addition, the locking member 42 also has a transversely curved recess 46, which is complementary to the curved transverse recess 40 in projecting end 38 and, when the locking member 42 is in parallel, abutting relationship with the projecting end 38, as shown in FIG. 3, the outer surface of the two members is circular in cross-section and complementary to a securing member 48, which is in the form of a cylindrical sleeve which is of limited length and is slidable along the barrel 10 between the releasing or unlocking position shown in FIG. 4 and the locking position shown in FIGS. 1–3. In the latter position, it securely connects the locking member 42 against the projecting end 38 of the forward end of barrel 10 and thereby secures the annular collar 36 of the cartridge 24 within the combined complementary curved transverse recess 40 and 46. When in this position, the longitudinal recess 44 in locking member 42 and the portion of the bore 14 in projecting end 38 of the barrel cooperate to receive the forward end of the projecting end 18 of plunger 16, for purposes of said forward end of the plunger being operable to project into the interior of the end of the cartridge 24 upon which the annular collar 36 is formed and either directly engage material therein or abut normally a closure plunger simply comprising a small plug in said end of the cartridge upon which the collar 36 is formed for purposes of sealing the contents of the cartridge until ready for use.

Figure 5:
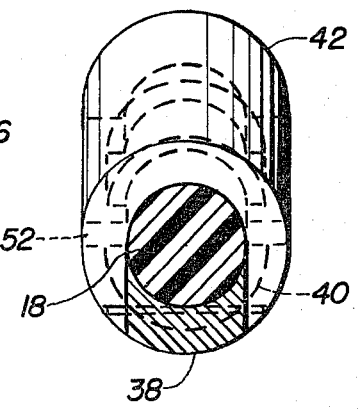
FIG. 5 is an enlarged transverse sectional view of the outer end portion of the holder shown in FIG. 4, as seen on the line 5—5 thereof and partially illustrating the pivoted means for one of the attaching members shown in FIG. 4.

For purposes of movably connecting the locking member 42 to the projecting end 38 of the barrel 10, the member 42 is provided with a pair of ears 50, which are disposed in appropriate recesses on opposite sides of the projecting end 38 of the barrel 10, and a transverse pivot pin 52, shown in FIGS. 4 and 5, extends through axially aligned transverse holes 54 in the ears 50 and another hole extending transversely through the projecting end 38 below the portion of the forward bore 14 in said projecting end, as shown best in FIG. 4, so as not to interfere with operation of the forward projecting end 18 of plunger 16.

To control the operation of sleeve 48 and limit the slidable movement thereof, the same is provided with a longitudinal slot 56 in which a limiting pin 58 is disposed and is firmly connected to a suitable bore in the forward portion of barrel 10, as best shown in FIGS. 3 and 4. The slot 56 is of appropriate length to permit movement of the sleeve 48 between the locking position shown in FIG. 3, and the releasing or unlocking position shown in FIG. 4.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. A manually-operable ejector holder for a loaded syringe-type cartridge provided with an annular collar on one end and a discharge tip on the other, said holder comprising in combination, an elongated barrel, a plunger reciprocable therein and one end thereof projecting beyond one end of said barrel, manually engageable means on said one end of said barrel operable to reciprocate said plunger toward and from the other end of said barrel, said other end of said barrel having a curved transverse recess positioned and operable to receive a portion of said collar on said cartridge, a locking member having one end pivotally connected to said barrel and also having a curved transverse recess complementary to said opposite recess in said other end of said barrel and operable to receive an opposite portion of said collar on said cartridge, and a securing member slidable over said locking member and along the other end of said barrel to releasably connect said cartridge to said holder and the other end of said plunger being slidable toward said cartridge in axial alignment with said collar of said cartridge to penetrate said cartridge and effect discharge to the contents thereof.

2. The holder according to claim 1 in which said other end of said barrel is cut away longitudinally a limited amount inward from said end for substantially half the diameter thereof to form a projecting end of half the depth of said barrel and said curved recess being formed in said projecting end, said locking member being complementary in transverse shape to said projecting end of said barrel and overlying the same when in locking position around the collar of said cartridge, and said securing member comprising a sleeve and the exterior of said locking member and projecting end each being semi-cylindrical and abutting each other to be received slidably within said securing sleeve.

3. The holder according to claim 2 in which said projecting end and locking member when in locking position have a combined interior axial bore to slidably receive said other end of said plunger.

4. The holder according to claim 2 in which the end of said locking member opposite its outer end is the end that is pivotally connected to said barrel to permit pivotal movement of the outer end of said locking member away from said projecting end to permit insertion and removal of said cartridge into and from said holder.

5. The holder according to claim 2 in which said securing sleeve has a slot of limited length therein and the outer end of a projecting pin secured to said barrel is disposed within said slot to limit the slidable movement of said sleeve between securing and release positions thereof for retaining or releasing said cartridge relative to said holder.

6. The holder according to claim 1 in which said other end of the barrel is cut away longitudinally a limited amount for substantially half the diameter of the barrel to form a projecting forward end on said barrel and said locking member being complementary in shape to said projecting end of the barrel and being disposed in said cut-away portion of the barrel and complementary in shape to said projecting end to form a cylindrical outer surface on said projecting end and locking member and also forming an interior bore when the same are in abutting position for locking, said locking member also having opposed ears extending along opposite surfaces of said projecting end of said barrel and a pivot pin extending through said ears and projecting end of said barrel at a location therein spaced from the portion of said bore in said projecting end of said barrel, and said securing member comprising a cylindrical sleeve slidable upon said barrel and also slidable over said projecting end of said barrel and locking member when the latter abuts said projecting end of the barrel in locking position to secure a cartridge to the forward end of said holder.

* * * * *